United States Patent
Schneider et al.

(10) Patent No.: US 11,417,329 B2
(45) Date of Patent: Aug. 16, 2022

(54) SYSTEM FOR PERFORMING A MAGNETIC RESONANCE TOMOGRAPHY AND METHOD FOR CONTROLLING AN MR SCANNER

(71) Applicant: Siemens Healthcare GmbH, Erlangen (DE)

(72) Inventors: Rainer Schneider, Erlangen (DE); Dirk Franger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 234 days.

(21) Appl. No.: 16/776,584

(22) Filed: Jan. 30, 2020

(65) Prior Publication Data

US 2020/0243090 A1 Jul. 30, 2020

(30) Foreign Application Priority Data

Jan. 30, 2019 (EP) .................................... 19154450

(51) Int. Cl.
*G10L 15/00* (2013.01)
*G10L 15/22* (2006.01)
(Continued)

(52) U.S. Cl.
CPC .............. *G10L 15/22* (2013.01); *A61B 5/055* (2013.01); *A61B 5/749* (2013.01); *G10L 15/30* (2013.01); *G10L 2015/223* (2013.01)

(58) Field of Classification Search
CPC .... G10L 15/22; G10L 15/223; A61N 1/37247
See application file for complete search history.

(56) References Cited

U.S. PATENT DOCUMENTS 5,345,538 A * 9/1994 Narayannan ............ G10L 15/26
704/270
5,544,654 A * 8/1996 Murphy .................... A61B 8/00
600/443

(Continued)

FOREIGN PATENT DOCUMENTS

CN 102855873 A 1/2013
JP 2009237439 A 10/2009

OTHER PUBLICATIONS

European Search Report dated Jul. 12, 2019, for Application No. 19154450.1.

*Primary Examiner* — Daniel Abebe
(74) *Attorney, Agent, or Firm* — Banner & Witcoff Ltd.

(57) ABSTRACT

A system for performing magnetic resonance tomography is disclosed. A control system creates a speech data stream from an acquired linguistic expression and generates a command library, which contains a selection of speech commands, to each of which one or more linguistic expressions are assigned. The selection of speech commands is loaded from a command database depending on a current system status of a magnetic resonance (MR) scanner. The control system applies a speech recognition algorithm to the speech data stream to determine whether a linguistic expression contained in the command library can be assigned to the speech data stream. If so, the acquired linguistic expression is recognized, a speech command from the command library assigned to the recognized linguistic expression is established, and a control command for controlling the MR scanner in accordance with the speech command is created.

9 Claims, 2 Drawing Sheets

Figure 1:
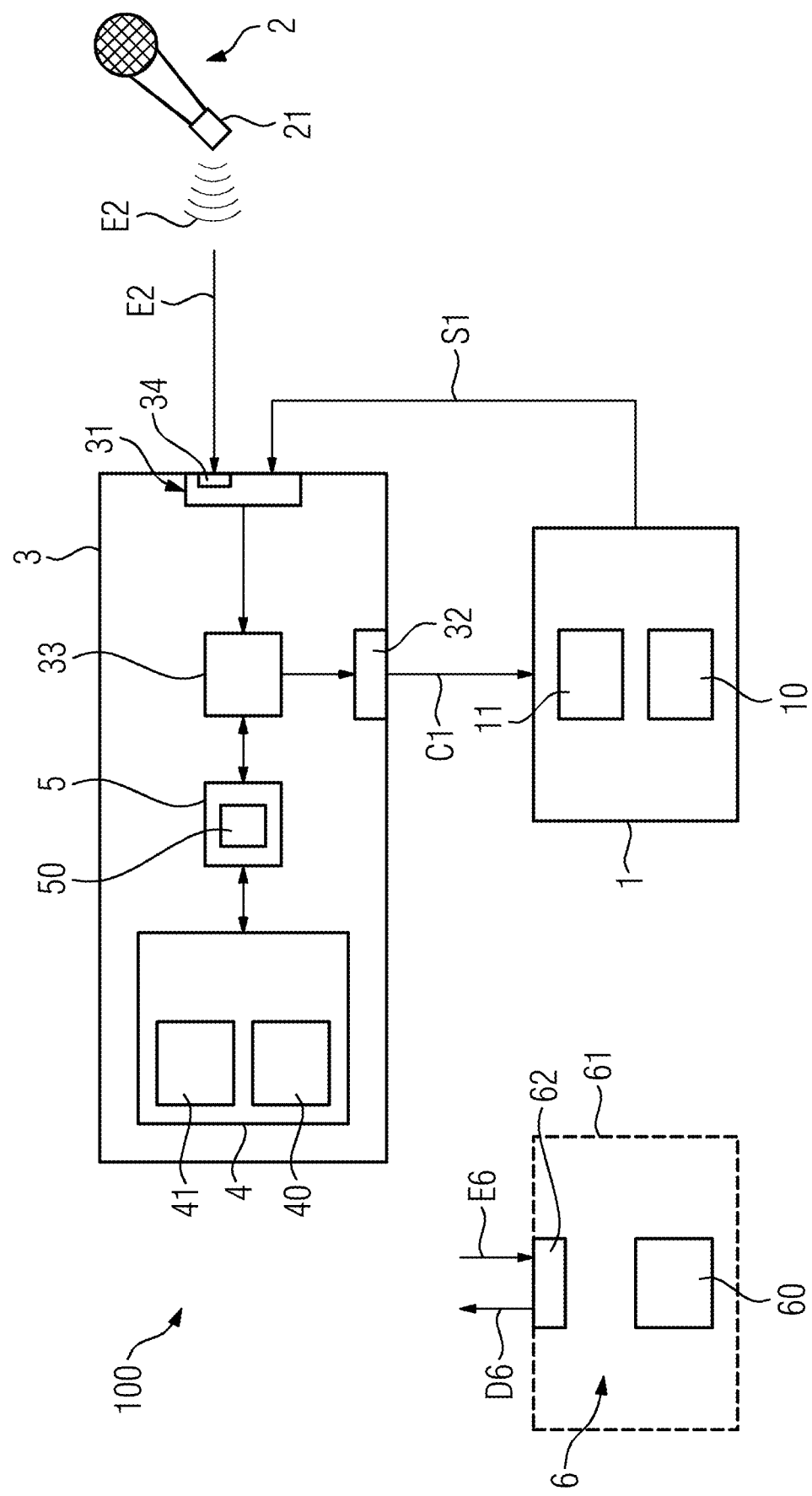

(51) Int. Cl.
   *A61B 5/055*   (2006.01)
   *A61B 5/00*   (2006.01)
   *G10L 15/30*   (2013.01)

(56) References Cited

U.S. PATENT DOCUMENTS

| | | | |
|---|---|---|---|
| 6,301,497 | B1 | 10/2001 | Neustadter |
| 6,304,848 | B1 * | 10/2001 | Singer .................... G16H 10/60 |
| | | | 705/3 |
| 7,319,962 | B2 * | 1/2008 | Goedeke ............ A61N 1/37247 |
| | | | 704/275 |
| 2001/0032085 | A1 * | 10/2001 | Goedeke ............ A61N 1/37247 |
| | | | 704/275 |
| 2002/0087357 | A1 * | 7/2002 | Singer .................... G16H 10/60 |
| | | | 705/2 |
| 2003/0068011 | A1 | 4/2003 | Johnson et al. |
| 2006/0020466 | A1 * | 1/2006 | Cousineau .......... G10L 15/1822 |
| | | | 704/257 |
| 2006/0220784 | A1 * | 10/2006 | Wang .................... A61B 34/70 |
| | | | 340/3.54 |
| 2016/0275950 | A1 | 9/2016 | Ogawa et al. |

* cited by examiner

SYSTEM FOR PERFORMING A MAGNETIC RESONANCE TOMOGRAPHY AND METHOD FOR CONTROLLING AN MR SCANNER

CROSS-REFERENCE TO RELATED APPLICATIONS

The present application claims the benefit of the filing date of European patent application no. 19154450.1, filed on Jan. 30, 2019, the contents of which are incorporated herein by reference in their entirety.

TECHNICAL FIELD

The disclosure relates to a system for performing a magnetic resonance (MR) tomography and a method for controlling an MR scanner.

BACKGROUND

Magnetic resonance tomography (MRT or alternatively simply MR), facilitates medical diagnosis as an imaging method in many situations. MR scanners, which have a coil arrangement for generating magnetic fields to create an image on the basis of the interaction of the magnetic fields with biological components of the area of the body of a patient to be examined, are used to perform a magnetic resonance tomography.

Various settings usually have to be made on the MR scanner before and during the performance of an MR examination of a patient, such as for example input of patient data, setting of various scan parameters, and the like. The patient also needs to be placed in the MR scanner. These steps are typically carried out by medical technicians, and the settings of the scanner are generally made partly via an interface provided on the MR scanner and partly via a computer located in a separate control room.

In order to operate MR systems economically, and to improve comfort for patients during the examination, a smooth working sequence or workflow is desirable. U.S. Pat. No. 6,301,497 describes an MR system in which specific functions of the scanner can be activated and deactivated with the aid of an input facility in the form of speech control.

SUMMARY

Against this background, a need arises to provide a concept for efficient operation of an MR system, e.g. a concept by which it is made easier to make settings on the system.

This object is achieved by the features of the independent claims and the various aspects of the disclosure as discussed herein. Advantageous aspects are additionally specified in the dependent claims.

In accordance with an aspect of the disclosure, a method is provided for controlling an MR scanner. In accordance with such aspects, a linguistic expression is acquired by means of an acoustic input, e.g. by the linguistic expression of an operator of the MR scanner being picked up by means of a microphone. From the acquired linguistic expression, a voice data stream is created via an analog-to-digital converter, for example. A current system status of the MR scanner is also established (e.g. determined). The system status is defined by the working steps that the MR scanner is carrying out. On the basis thereof, the system status comprises information about or defines the operations or working steps that the scanner could potentially carry out, using the current status as a starting point.

In a further step, a library of commands is generated, which contains a selection of (e.g. a set of) speech commands to each of which one or more linguistic expressions are assigned. A speech command, which can also be referred to as an "intent," can be understood as a computer-readable dataset that contains information about the control command by which the MR scanner is to be actuated. A speech command and one or more expressions, e.g. a number of synonymous terms or expressions with different sequences of words, are assigned to one another in the command library in each case. In accordance with the present aspects, the selection of speech commands is loaded from a command database depending on the current system status of the MR scanner. This means that a check is made as to the system status obtaining in the MR scanner and, depending on the system status, a specific group of speech commands is loaded from the command database into the temporary command library or the command library is temporarily constructed from this group of speech commands. For example, each system status can be assigned a predetermined group of speech commands in the command database. For instance, this group can be composed only of speech commands that are able to be used to create a control command that the scanner can actually carry out in its system status.

In a further step, a speech recognition algorithm is applied to the speech data stream to establish whether a linguistic expression contained in the command library is able to be assigned to the speech data stream, and there is a recognition of (e.g., identification of) the acquired linguistic expression if a linguistic expression contained in the command library is able to be assigned to the speech data stream. The speech recognition algorithm can be realized as software, for example.

Furthermore, a speech command assigned to the linguistic expression recognized from the command library is established. Thus, in this step there is a selection of the speech command that is assigned to the expression recognized. Finally, a control command for controlling the MR scanner in accordance with the speech command established is created. The control command can be, for example, an electrical signal that causes the MR scanner to carry out a predetermined working step, e.g. to create a magnetic field with a specific field strength.

In accordance with another aspect of the disclosure, a non-volatile, computer-readable data storage is provided, which stores a software program that is configured to cause a computer to carry out the steps of a method as further described herein, such as in accordance with one of the above aspects, for instance. The non-volatile data storage can be implemented, for instance, as a non-transitory computer-readable medium such as a hard disk, a CD-ROM, a DVD, a Blu-Ray disk, a diskette, a flash memory, or the like.

In accordance with another aspect of the disclosure, a system for performing a magnetic resonance tomography is provided. The system comprises an MR scanner for performing a scan sequence on a patient, an acoustic input for acquiring a linguistic expression and a control system with an input which is connected to the acoustic input and to the MR scanner, and an output, which is connected to the MR scanner. The control system thus has a first interface as an input and a second interface as an output, with the first and the second interface each being configured for wired or wireless data exchange and can be implemented, for example, as a bus interface, as a Wi-Fi interface, or in a similar manner The input device and the MR scanner are each in data communication with the input of the control system. The MR scanner is also connected to the output for exchange of data. The input and the output can be realized here by physically separate connections or interfaces, or can be realized as a common connection.

In accordance with the aspects of the disclosure, the control system is configured to create a speech data stream from the acquired linguistic expression, to establish a current system status of the MR scanner, to generate a command library that contains a selection of speech commands, to each of which one or more linguistic expressions are assigned, wherein the selection of speech commands is loaded from a command database depending on the current system status of the MR scanner, to apply a speech recognition algorithm to the speech data stream to establish whether a linguistic expression contained in the command library is able to be assigned to the speech data stream, to recognize the acquired linguistic expression if a linguistic expression contained in the command library is able to be assigned to the speech data stream, to establish a speech command from the command library assigned to the recognized linguistic expression and to create a control command for controlling the MR scanner in accordance with the speech command.

In general, the system aspects can be provided and be configured to carry out the method aspects of the disclosure. The features and advantages disclosed in conjunction with the method aspects of the disclosure are therefore also disclosed and are also applicable for the system aspects of the disclosure, and vice versa.

An idea underlying the disclosure consists of realizing speech control for controlling an MR scanner. For instance, dynamically, depending on the current system status or the actual status in which the MR scanner finds itself, a library with speech commands available for the status is generated. This offers the advantage that the number of expressions that are supplied together with the speech data stream to the speech recognition algorithm as input variables or input data is reduced compared to the number of expressions that are contained in the speech command database. In this way, the computing power that is needed to execute the speech recognition algorithm is advantageously reduced.

A further advantage lies in the fact that the reliability of the speech recognition is improved by the reduced number of expressions in the library. This is of particular advantage since MR scanners typically generate loud noises, which makes it more difficult to recognize speech commands Through the dynamic reduction of the selection options, the speech control becomes more robust, and the susceptibility to faults is reduced. In this way, the working sequence at the MR scanner is sped up, since the operating personnel can efficiently control the scanner by speech commands. The speech recognition additionally offers the advantage that it is done without physical, e.g. without manual interaction with the input device, whereby hygiene benefits are obtained.

In accordance with the method aspects, there is provision that, when the speech data stream is not able to be assigned to any linguistic expression contained in the command library, the speech data stream is supplied to (e.g., transmitted to) an Internet-based online speech recognition module, wherein the online speech recognition module applies a recognition function trained by machine learning to the input data stream and provides (e.g. outputs) a recognized linguistic expression as the output data stream. Accordingly, if the speech recognition algorithm cannot assign the speech data stream to any linguistic expression contained in the command library, a computer-implemented algorithm trained by machine learning is used. This online speech recognition module can, for example, obtain data for a plurality of MR systems via the Internet. This further improves the application-specific reliability of speech recognition.

When a specific linguistic expression has been recognized by means of the online speech recognition module, there can be an optional check as to whether the recognized linguistic expression is assigned to a speech command in the command library. If it is, the method can be continued as described above. The operation of the MR scanner is made easier by this, since the inadvertent input of incorrect speech commands is avoided.

One or more of the following states can be established as the current system status of the MR scanner as follows:
a) the MR scanner is in a standby operating mode;
b) the MR scanner is performing a predetermined scan sequence;
c) the MR scanner is in a pause state, in which the performance of a predetermined scan sequence is interrupted;
d) the MR scanner is in a preparation state for carrying out a predetermined scan sequence.

If it is established for example that the MR scanner is currently in state b), the speech command library can be assembled in such a way that, for instance, said library only contains speech commands in accordance with which a control command will be created that causes the MR scanner to stop the scan sequence. In state b) the system status can further be defined by the type of scan sequence that is being executed. Through this, it can be determined for example whether specific setting parameters of the sequence can be read/changed. Starting from the system status, the sequences that can be opened, changed, and started are determined, for example.

In accordance with an aspect, there can be provision for the command database to be stored on the data storage device. This offers the advantage of especially fast access to the speech commands and the associated expressions, which further speeds up and facilitates the recognition.

In accordance with an aspect, the acoustic input includes a microphone.

In accordance with a further aspect, there is provision for the acoustic input to be portable and to have a transmitter for wireless data transmission, wherein the input of the control system has a receiver for wireless data transmission that communicates with the transmitter of the acoustic input. This offers the advantage of the acoustic input being able to be arranged physically separated from the control system, which further facilitates the work sequences at the MR scanner.

In accordance with a further aspect, the control system has the non-volatile data storage in accordance and a processor for reading the data storage.

A "processor" may be understood as an electronic circuit for computer-based data processing, for example a CPU. It can involve the CPU of a computer or a microprocessor of a microchip, a controller, etc. The processor can further also be realized, as examples, as a field-programmable gate array (FPGA) or as an application-specific integrated circuit (ASIC).

BRIEF DESCRIPTION OF THE DRAWINGS/FIGURES

Figure 2:
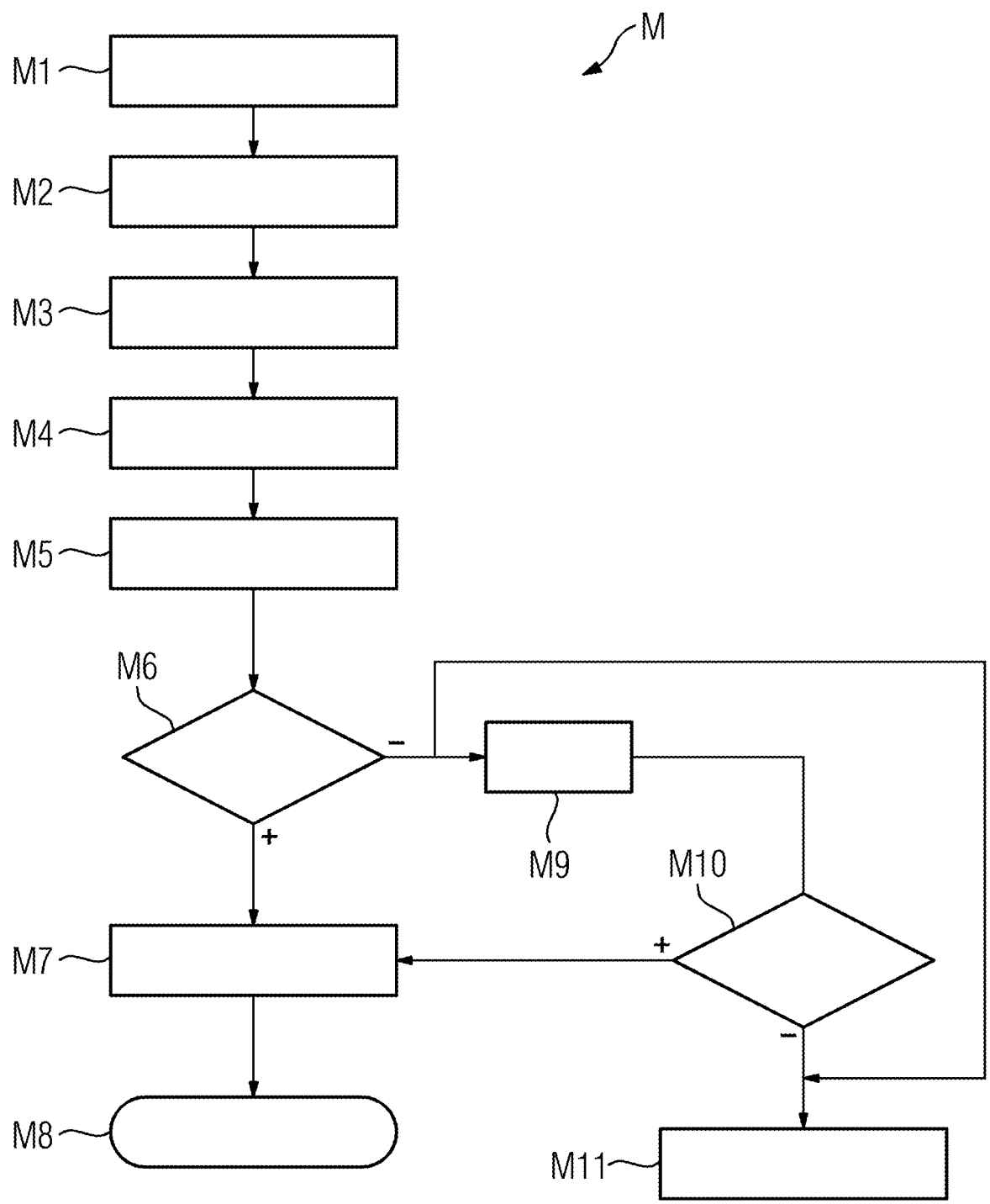

The disclosure will be explained below in greater detail on the basis of exemplary aspects with the aid of the Figures. In the figures:

FIG. 1 shows a schematic diagram of an exemplary system for performing a magnetic resonance tomography, in accordance with an aspect of the present disclosure; and FIG. 2 shows a flow diagram of an exemplary method for controlling an MR scanner, in accordance with an aspect of the present disclosure.

DETAILED DESCRIPTION

FIG. 1 shows a schematic of a functional block diagram of a system 100 for performing a magnetic resonance (MR) tomography. The system 100 comprises an MR scanner 1, an acoustic input 2, and a control system 3. Also shown as a block in FIG. 1 is an online speech recognition module 6, which is able to be connected to the system 100.

The MR scanner 1 is configured for carrying out a scan sequence on a patient, and is not explained in any greater detail in this document. In particular, the MR scanner 1 can have a generator circuit 10 for generating a static magnetic field and for creating magnetic alternating fields in the radio frequency range, with which specific atomic nuclei are resonantly excited in the body of the patient, and a receiver circuit 11, in which an electrical signal is able to be induced in the body of the patient by excitation of the atomic nuclei.

The acoustic input 2 serves to pick up or to acquire a linguistic expression E2, i.e. to pick up spoken sounds that are created by an operator. The acoustic input 2 can be realized as any suitable device suitable for this purpose, such as a microphone, for example. The acoustic input 2 can be arranged in a stationary manner on the MR scanner 1 or at another location, such as in an operating room, for example. As an alternative, the acoustic input 2 can be realized as a portable device, e.g. as a microphone of a headset that the operator can carry around. In such a case, the acoustic input 2 advantageously has a transmitter 21 for wireless data transmission.

The control system 3 has an input 31 for receiving signals, and an output 32 to generate or output signals. The control system 3 is generally configured to carry out data processing operations and to create electrical signals. To this end, the control system 3 can have a processor 33, e.g. in the form of a CPU or the like, and a data storage 4, e.g. a non-volatile data storage (e.g. a non-transitory computer-readable medium) able to be read by the processor 33, such as a hard disk, a CD-ROM, a DVD, a Blu-Ray disk, a diskette, a flash memory or the like. Software 40, 41, which is configured to cause the processor 33 to carry out the steps of a method (e.g., the method further described below with reference to FIG. 2), which can be stored on the data storage 4.

As is shown schematically in FIG. 1, the input 31 of the control system 3 is connected to the acoustic input 2 and to the MR scanner 1. The input 31 can be configured for wireless or for wired data communication. For example, the input 31 can have a bus connection. Additionally or alternatively to a wired connection, the input 31 can also have an interface, e.g. a receiver 34 for wireless data transmission. For example, as shown in FIG. 1, the receiver 34 can be in data communication with the transmitter 21 of the acoustic input 2. Any suitable communication interface configured to receive transmitted information, such as a Wi-Fi interface, a Bluetooth interface, or the like can be provided as the receiver 34, for example.

The output 32 of the control system 3 is connected to the MR scanner 1. The output 32 can be configured for wireless or for wired data communication. For example, the output 32 can have a bus connection. As an alternative or in addition to a wired connection, the output 32 can also implement any suitable communication interface configured for wireless data transmission, for example a Wi-Fi interface, a Bluetooth interface, or the like.

The control system 3 is configured to create a control command C1 to control the MR scanner 1 and to provide the control command at the output 32. The control command C1 causes the MR scanner 1 to carry out a specific working step or a sequence of steps, for example to carry out a specific scan sequence with a specific excitation of magnetic fields by the generator circuit 10.

The MR scanner 1 is controlled in the system 100 depicted by way of example in FIG. 1 by a method M for example, which is shown in FIG. 2 by way of example as a flow diagram. In general, the operator (not shown), who is operating the MR scanner 1 may express a command with their voice or by speech, e.g. by speaking a sentence such as "start scan sequence X," for the acoustic input 2 to acquire this linguistic expression E2 and for the control system 3 to analyze the linguistic expression E2 and to create a corresponding control command C1 for actuating the MR scanner 1. An advantage of this process is that the operator can also handle other tasks while speaking, e.g. deal with getting the patient ready. This advantageously speeds up the work sequences. The MR scanner 1 can further be controlled at least partly "without touching it" or without physical (i.e. touch-based) interaction, whereby hygiene at the MR scanner 1 is improved.

As shown in FIG. 2 by the block M1, there is first an acquisition of the linguistic expression E2 by means of the acoustic input 2. This linguistic expression E2 is made available to the control system 3 at the input, and the control system 3 creates from the acquired linguistic expression E2 a speech data stream (block M3). To this end, an analog-digital converter (not shown) can be provided, for example. The creation of the speech data stream can optionally comprise a step in which a start and an end of the linguistic expression within a spoken sequence of expressions is detected. This can be realized by software for example, which is stored on the data storage 4 and causes the processor 33 to carry out this step. In this case, the acquired linguistic expression E2 is extracted as the speech data stream from the overall data stream that contains the sequence of expressions.

As shown symbolically in FIG. 2 by block M3, a current system status S1 of the MR scanner 1 is established (M3) in a further step. The system status S1 of the MR scanner S1 can be given, for example, by a standby operating mode of the MR scanner 1 or by the fact that the MR scanner 1 is executing a predetermined scan sequence or is in a preparation state for executing a predetermined scan sequence. Generally, the system status S1 is determined by a respective working step or by a series or sequence of working steps that the MR scanner is executing. This produces, as a result, the further working steps that the scanner 1 could potentially execute and thus how it can be actuated. For example, the system status can be supplied as an input value to a look-up table, in which information for the various system states necessary for the activation of the MR scanner 1 is contained. The MR scanner 1 provides this system status S1 to the control system 3 at input 31, e.g. as a data signal.

In a further step M4, a command library 50 is generated, which contains a selection of speech commands, to which one or more linguistic expressions are assigned in each case, wherein the selection of speech commands is loaded from a command database 40 depending on the current system status S1 of the MR scanner. The command library 50 is generated temporarily for a respective system status S1, and can be loaded for example as a temporary file into a working memory 5 of the control system 3. The content of the command library 50, i.e. the individual datasets in which a speech command is linked to one or more linguistic expressions in each case, is loaded from a command database 40, which can be stored on the data storage 4, for example. The datasets that can be loaded from the command database 40 into the command library 50 depend on the system status S1 of the MR scanner 1. For example, the MR scanner 1, when executing a specific scan sequence, can only execute specific steps or further working steps. This information is held in the command database 40 together with a speech command that brings about the creation of a control command C1 corresponding to the working step. Thus, in step M4, a selection of speech commands for the system status S1 of the MR scanner present in each case is loaded from a command database 40.

In step M5, there is an application M5 of a speech recognition algorithm to the speech data stream to establish whether the speech data stream is able to be assigned to a linguistic expression contained in the command library 50. The speech recognition algorithm can be contained on the data storage 4, as software 41 for example. When a linguistic expression contained in the command library 50 is able to be assigned to the speech data stream, in step M6 the acquired linguistic expression E2 is recognized, as is shown symbolically in step M6 as "+." In steps M5 and M6, it is thus decoded (e.g. determined) whether the acquired linguistic expression E2, which has been converted into the speech data stream, matches an expression contained in the command library 50. This functions especially reliably in the described method M, since only a limited number of expressions are contained in the command library 50, namely only those that belong to the speech commands possible for the respective system status S1 of the scanner 1. Thus, the reliability of the speech recognition is improved.

In step M7, which is carried out if in step M6 the acquired linguistic expression E2 was recognized (symbol "+" in FIG. 2), a speech command assigned to the recognized linguistic expression is established from the command library 50. This can be supplied in the form of an input variable for example to a creation module of software, which is stored on the data storage 4 for example, which then causes the processor 33 to create (step M8) a control command C1 for controlling the MR scanner in accordance with the speech command.

If, in step M6, the acquired linguistic expression E2 was not recognized (symbol "–" in FIG. 2), because no linguistic expression contained in the command library 50 is able to be assigned to the speech data stream, the method M may end (step M11). Optionally, a further step M9 can be carried out, as shown in FIG. 2. Here, the speech data stream is supplied to an Internet-based online speech recognition module 6 as input data stream E6. The online speech recognition module 6 can be stored on a server 61 with which the control system 3 can enter into an exchange of data via an Internet connection.

The online speech recognition module 6 can have a recognition function 60 trained by machine learning as its software, which is applied to the input data stream E6 and provides a recognized linguistic expression as output data stream D6 at an interface 62 of the server 61. This output data stream D6 can be supplied to the control system 3 via the input 31, for example. In an optional further step M10, a check is then made as to whether the recognized linguistic expression is assigned to a speech command in the command library 50, as has already been described above with reference to step M6. If, in step M10, the acquired linguistic expression E2 was recognized (symbol "+" in FIG. 2), then the steps M7 and M8 are carried out as described above. If the linguistic expression E2 was not recognized in step M10, as is shown in FIG. 2 by the symbol "–", the method ends (block M11).

In steps M3 to M8, without carrying out the optional steps M9 and M10, there is a speech-based control of the MR scanner 1, in which speech commands are linked to a limited selection of linguistic expressions that are stored in the command database 40. This is especially advantageous in conjunction with MR systems, since the linguistic expressions often involve medical technology jargon. Moreover, through the provision of the expressions in a database, an adaptation to customer wishes is facilitated, since the expressions that are linked to a specific speech command can be readily changed. For example, the customer or the operating personnel can re-name the expressions for a speech command themselves.

The optional steps M9 and M10 further improve upon the reliability of the control, in that an algorithm trained by machine learning may be implemented to recognize the acquired expression. The algorithm may have been trained, for example, by a plurality of expressions that have been spoken by various people and/or which were picked up together with various typical MR background noises, etc.

Although the present disclosure has been illustrated and described in greater detail by the exemplary aspects, the disclosure is not restricted by the disclosed examples, and other variations can be derived herefrom by the person skilled in the art without departing from the scope of protection of the disclosure.

What is claimed is:

1. A method for controlling a magnetic resonance (MR) scanner, the method comprising:
   determining a current system status of the MR scanner;
   receiving, via an acoustic input, a spoken linguistic expression;
   generating a first speech data stream from the acquired linguistic expression;
   generating a command library that contains a set of speech commands, each of the set of speech commands being assigned to one or more linguistic expressions, the set of speech commands being loaded from a command database depending on the determined current system status of the MR scanner;
   determining, via application of speech recognition to the first speech data stream, whether a linguistic expression contained in the command library is able to be assigned to the first speech data stream;
   when the linguistic expression contained in the command library is able to be assigned to the first speech data stream:
     identifying the acquired linguistic expression;
     determining a speech command from among the set of speech commands in the command library that is assigned to the recognized linguistic expression; and
     generating a control command to control the MR scanner in accordance with the determined speech command; and
   when no linguistic expression contained in the command library is able to be assigned to the first speech data stream:
     transmitting the first speech data stream to an Internet-based online speech recognition system; and
     applying, via the Internet-based online speech recognition system, a machine learning trained recognition function to the first speech data stream to provide a recognized linguistic expression as a second speech data stream.

2. The method as claimed in claim 1, further comprising: determining whether the recognized linguistic expression provided as the second speech data stream is assigned to a speech command in the command library.

3. The method as claimed in claim 1, wherein the current system status of the MR scanner includes the MR scanner being in one or more of the following states:
   a standby operating mode;
   a predetermined scan sequence;
   a pause state in which execution of a predetermined scan sequence is interrupted; and
   a preparation state for executing a predetermined scan sequence.

4. A non-transitory, computer readable medium having instructions stored thereon that, when executed by one or more processors of a magnetic resonance (MR) scanner, cause the MR scanner to:
   determine a current system status of the MR scanner;
   receive a spoken linguistic expression via an acoustic input;
   generate a first speech data stream from the acquired linguistic expression;
   generate a command library that contains a set of speech commands, each of the set of speech commands being assigned to one or more linguistic expressions, the set of speech commands being loaded from a command database depending on the determined current system status of the MR scanner;
   determine, via application of speech recognition to the first speech data stream, whether a linguistic expression contained in the command library is able to be assigned to the first speech data stream;
   when the linguistic expression contained in the command library is able to be assigned to the first speech data stream:
      identify the acquired linguistic expression;
      determine a speech command from among the set of speech commands in the command library that is assigned to the recognized linguistic expression; and
      generate a control command to control the MR scanner in accordance with the determined speech command; and
   when no linguistic expression contained in the command library is able to be assigned to the first speech data stream:
      transmitting the first speech data stream to an Internet-based online speech recognition system; and
      applying, via the Internet-based online speech recognition system, a machine learning trained recognition function to the first speech data stream to provide a recognized linguistic expression as a second speech data stream.

5. The non-transitory, computer readable medium as claimed in claim 4, wherein the non-transitory, computer readable medium further includes instructions representing storage of the command database.

6. A system for performing a magnetic resonance (MR) tomography, comprising:
   an MR scanner configured to execute a scan sequence on a patient;
   an acoustic input configured to receive a spoken linguistic expression; and
   a control system having an control input and a control output, the control input being coupled to the acoustic input and to the MR scanner, and the control output being coupled to the MR scanner, the control system being configured to:
      determine a current system status of the MR scanner;
      generate a first speech data stream from the acquired linguistic expression;
      generate a command library that contains a set of speech commands, each of the set of speech commands being assigned to one or more linguistic expressions, the set of speech commands being loaded from a command database depending on the determined current system status of the MR scanner;
      determine, via application of speech recognition to the first speech data stream, whether a linguistic expression contained in the command library is able to be assigned to the first speech data stream;
      when the linguistic expression contained in the command library is able to be assigned to the first speech data stream:
         identify the acquired linguistic expression;
         determine a speech command from among the set of speech commands in the command library that is assigned to the recognized linguistic expression; and
         generate a control command to control the MR scanner in accordance with the determined speech command; and
      when no linguistic expression contained in the command library is able to be assigned to the first speech data stream:
         transmitting the first speech data stream to an Internet-based online speech recognition system; and
         applying, via the Internet-based online speech recognition system, a machine learning trained recognition function to the first speech data stream to provide a recognized linguistic expression as a second speech data stream.

7. The system as claimed in claim 6, wherein the acoustic input includes a microphone.

8. The system as claimed in claim 6, wherein the acoustic input is portable and includes a transmitter configured to wirelessly transmit data, and
   wherein the control input includes a receiver configured to wirelessly receive data transmitted via the transmitter of the acoustic input.

9. The system as claimed in claim 6, wherein the control system includes a data storage device and a processor configured to read data stored on the data storage device.

* * * * *